United States Patent [19]

Franzen

[11] Patent Number: 5,595,636
[45] Date of Patent: Jan. 21, 1997

[54] METHOD FOR MASS SPECTROMETRIC ANALYSIS OF SAMPLES FROM ELECTROPHORESIS PLATES

[75] Inventor: Jochen Franzen, Bremen, Germany

[73] Assignee: Bruker-Franzen Analytik GmbH, Bremen, Germany

[21] Appl. No.: 401,404

[22] Filed: Mar. 9, 1995

[30] Foreign Application Priority Data

Mar. 10, 1994 [DE] Germany ............... 44 08 034.4

[51] Int. Cl.$^6$ .................. G01N 27/26; G01N 27/447
[52] U.S. Cl. .................. 204/464; 204/462; 204/613; 204/614
[58] Field of Search .................. 204/229 R, 182.8, 204/180.1, 462, 464, 613, 614

[56] References Cited

U.S. PATENT DOCUMENTS 5,260,571  11/1993  Cottrell et al. .................. 250/288

FOREIGN PATENT DOCUMENTS 2235528  3/1991  United Kingdom .
2235529  3/1991  United Kingdom .

OTHER PUBLICATIONS

Kerstin Strupat et al., *Matrix–Assisted Laser Desorption Ionization Mass Spectrometry of Proteins Electroblotted after Polyacrylamide Gel Electrophoresis*, Analytical Chemistry, vol. 66, pp. 464–470, No. 4, Feb. 14, 1994.

Martha M. Vestling and Catherine Fenselau, *Poly (vinylidene diflouride) Membranes as the Interface between Laser Desorption Mass Spectrometry, Gel Electrophoresis and in Situ Proteolysis*, Analytical Chemistry, vol. 66, No. 4, pp. 471–477, Feb. 15, 1994.

*Primary Examiner*—Arun S. Phasge
*Assistant Examiner*—John S. Starsiak, Jr.

[57] ABSTRACT

The invention relates to the mass spectrometric analysis of separated substance samples on so-called 2-D-gel electrophoresis plates, used particularly for protein determination, with ionization of the substance samples by MALDI. The molecules of the substance samples are transferred to a thin, lacquer-like smooth matrix layer which should preferably be applied to a metal sample support. Transfer takes place directly or indirectly, for example via a polyvinylidene difluoride membrane an an intermediate carrier, by electrophoretic transport of the molecules to the matrix surface. Before transfer, the proteins may be subjected to enzymatic cutting of their amino acid chains.

15 Claims, No Drawings

METHOD FOR MASS SPECTROMETRIC ANALYSIS OF SAMPLES FROM ELECTROPHORESIS PLATES

BACKGROUND OF THE INVENTION

1. Field of the Invention

This invention relates to the field of mass spectrometry and, more specifically, to the mass spectrometric analysis of samples resulting from an electrophoresis process.

2. Description of the Related Art

Two-dimensional electrophoresis constitutes one of the fastest and neatest methods of separating hundreds of proteins simultaneously from biological protein compounds and also offers an approximate classification. In the monthly journal "Electrophoresis" (published by Verlag Chemie, Weinheim), in annual special November issues, thousands of human and animal proteins which have been separated and approximately classified are compiled in databases. An approximate determination of the molecular weight of the proteins due to the electrophoretic properties is performed which, however, may be incorrect by a factor of 2 on account of unknown form factors. The molecular weights range from 8 to about 160 kilodalton.

Of the 3,038 skin proteins published in November 1993, 763 were more closely identified, and of 176 proteins only parts of the amino acid sequence were known. The same is true, in principle, for the databases previously published. In total it can be estimated that the number of human proteins is between 50,000 and 100,000.

It is desirable to determine the proteins more accurately. In particular, the "Human Genome Project" would run idle if it were not possible to determine the proteins generated by the DNA chains accurately. Determination should not be restricted only to the exact molecular weight but preferably also to the determination of the complete amino acid sequence irrespective of DNA sequence analyses.

Determining the molecular weights of the original proteins, of their tryptic fragments, and of collisional ion fragments can be performed quickly and easily with mass spectrometry. Matrix-assisted laser desorption/ionization (MALDI) permits the highly effective ionization of peptides and proteins, even simultaneously in mixtures. MALDI—is already a widespread standard technique. It is used predominantly for time-of-flight mass spectrometry but it is also suitable for ion-storage mass spectrometers such as ICR spectrometers or ion traps.

In the MALDI method, bombardment with a pulsed laser heats a small volume of matrix substance and creates a cloud of vapour which contains a small proportion of ionized molecules and thus constitutes a weak plasma. The large molecules enclosed in the matrix material, that is the proteins, are thereby co-evaporated without causing damage. The heavy molecules in this plasma are preferentially ionized by ion molecule reactions because their ionization is energetically more favourable.

MALDI is particularly favourable for time-of-flight mass spectrometers because the ions of the large molecules are created in a very short time interval, and because time-of-flight spectrometers are particularly suitable for the examination of large molecules. Usually lasers with a pulse length of approximately 5 nanoseconds are used.

So far, the method has principally used layers with a very irregular surface consisting of matrix crystals of greatly different size into which the substance has to be embedded. However, newer methods have become known, not having these disadvantages.

Great Britain Patent Application 2,235,528 in particular describes a method in which a thin film of matrix material is applied to a mass spectrometer target, followed by a solution containing the sample substance. Various methods are described for the application of the matrix, for example electrospraying, aerosol spraying, spin coating, and evaporation. The sample is applied to the dry matrix as drops of sample in solution. The use of a solvent for the sample substance is somewhat undesirable, as such solvents tend also to dissolve the matrix layer.

The idea of subjecting electrophoretically separated proteins to MALDI analysis is not new. In fact, recently two papers were published which deal with MALDI ionization of electro-blot membranes with subsequent application of the matrix materials.

K. Strupat, M. Karas, F. Hillenkamp, C. Eckershorn, and F. Lottspeich (Anal. Chem. 66, 464, (1994)) report the use of the MALDI ionization technique in the analysis of peptides which had been transferred from gel plates to PVDF membranes by electrophoresis and subsequently coated with matrix substances. Laser desorption took place from the PVDF membrane direct. With various matrices both UV laser light (337 nm) and infrared light (2.94 μm) were used, the latter producing better results. However, ionization from the PVDF membrane had considerable drawbacks. In the lower mass range, large quantities of background ions appeared not resolved as lines, covering the scan of small peptides.

M. Vestling and C. Fenselau (Anal. Chem. 66,471 (1994)) report a practically identical method with UV light (337 nm), with additional enzymatic breakdown of the proteins by proteolysis in the PVDF membrane. Due to better sample preparation, probably as a result of improved washing, better scans were obtained. This work also offers a good overview of the current state of the art.

In both cases the mass resolutions obtained are by no means as good as obtained with thin layer matrix films even if the authors report "satisfactory levels of accuracy of 0.1%" for the mass determination. An accuracy of 0.1% is not sufficient to determine the molecular mass in the mass range from 1,000 to 3,000 atomic units of mass with absolute certainty.

SUMMARY OF THE INVENTION

In accordance with the invention, there is provided a method for the mass spectrometric analysis of an analyte substance in a sample which has been separated by gel electrophoresis on a gel electrophoresis plate, which method comprises transferring the sample to a sample support plate and ionising the analyte substance by means of matrix assisted laser desorption ionization, wherein the sample support plate is coated with a smooth adsorptive layer of a solid matrix substance and wherein the sample is transferred to the surface of the matrix layer of the sample support plate by direct contact with the moist electrophoresis plate, or by contact with a moist transfer membrane.

The term "matrix" as used herein is intended to mean a material which can be co-evaporated with the analyte, and which interacts with the analyte in the gaseous phase so as to generate ions of the analyte by ion-molecular reactions. The term "matrix" is not intended to imply that the analyte is embedded within crystals of the matrix as in the conventional MALDI method described above. Materials suitable for forming a matrix for use in such methods are well known, and are described, for example in the Strupat et al and Vestling et al papers referred to above.

In accordance with the invention, a microscopically smooth layer (by which is meant a layer of which surface fluctuations preferably do not exceed 1 micrometer in height, and which is preferably optically smooth) is made of the matrix substance and that layer is adsorptively loaded with the analyte substance.

Proteins and other analytes can be applied to matrix layer subsequently to its preparation, without embedding into the matrix material. The term "protein" as used herein is intended to be understood in its broadest sense to include any polypeptide-containing molecule, including, for example glycoproteins and other peptide containing molecules. Subsequently they can be ionized very efficiently by a process very similar to conventional MALDI except that the sample substance molecules are not embedded. The process exhibits a high sensitivity and a scan quality not achieved hitherto. Hitherto, the general view has been that the analyte had to be integrated into crystals of the matrix substance during crystallization to render it capable of being ionized by laser desorption.

It is found that analytes from solutions of which the solvent does not substantially dissolve the matrix substance firmly bind themselves to the matrix. The surface of the matrix is capable of binding mobile analyte molecules from the solution by diffusion.

It is found that this process of binding to the matrix surface is not impaired by buffer salts present, and not even by weak acids.

Matrix layers with the proteins applied can be subsequently washed without losing the proteins. Consequently, salts, electrolytes, and other additives to the protein solution can be removed from the matrix layer. These washing processes are extremely important because they bring about an increase in quality of the scans obtained. Some of the peptides only appear after washing, some appear only as cation adducts without washing, and some appear as normally protonated ions. All in all, the resolving power is reduced without washing processes. (Matrix layers made according to the conventional method of out-crystallization from applied droplets are unable to withstand washing processes; the minute crystals are washed away.)

In the method of the invention the adsorption power of such a matrix layer is used to bind diffusing or wandering sample molecules separated by and distributed over a 2D electrophoresis plate.

DETAILED DESCRIPTION OF THE PREFERRED EMBODIMENTS

In the most simple embodiments of the invention, the moist gel of the electrophoresis plate is simply brought into direct contact with the smooth matrix layer. By this method, analyte molecules which reach the matrix layer by diffusion will immediately be bound to it. For electrophoresis plates heavily loaded with sample molecules, this simple method will be sufficient.

Unfortunately the molecules are not sufficiently mobile in the gel layer for them to diffuse to any very great extent. For this reason only very small quantities of the analysis substances can be applied to the matrix layer without additional measures.

In a preferred embodiment, the analyte is transferred to the matrix by direct contact with a transfer membrane, to which the proteins can be transferred by the familiar method of so-called "electro-blotting", i.e. by electrophoretic transport. However, in this method also the protein molecules on the transfer membrane are not freely mobile, although they do occur in a higher concentration at the surface.

It is known to employ diffusion adjuvants to detach the protein from the gel or from the transfer membrane, making it more mobile, and thus improve attachment to the matrix layer. It is well-known that trifluoroacetic acid in a very diluted form can be used for this purpose. Disadvantageously, the local resolution of the separation deteriorates.

A greatly improved method uses electrophoretic transport of the protein molecules to the matrix layer, at which they are bound in the manner described above. The transport may be enhanced by certain electrolytes such as weak solutions of tris-base or boric acid. The technique is already widespread in biochemistry and does not need to be explained in detail.

Electrophoretic transport calls for a minimal flow of current through the thin microcrystalline matrix layers. Some layers require an artificial increase in conductivity. This can be caused by inlaying conductive substances, for example ionic conductors (salts) and metallic conductors (very fine metal powders).

By utilising an intermediate support such as a polyvinylidene difluoride (PVDF) membrane the protein chains can also be cleaved by enzymes in a conventional manner by proteolysis. Again, this technique is known in the biochemical field.

In all these techniques the washing of the matrix-loaded sample support is of great importance. The salts utilised for electrophoretic separation in the gel and the electrolytes required for the electrophoretic transport to the blot membrane or to the matrix layer (for example boric acid) have to be washed off again in order to obtain scans of the aforementioned excellent quality.

When proteins are applied to the matrix layer and washed in this way mass scans of excellent quality are produced. They may be isotope-resolved up to a molecular weight range of 3,000 Dalton, that is, the mass signals of the individual masses of the isotope sample of a molecule can be separated from one another and for the individual masses accurate mass numbers can be determined. The accuracy of mass determination can be as high as 20 ppm. The sensitivity of the method is also excellent. It is possible to obtain scans which can be readily measured of 50 attomol of a peptide or protein.

The method of the invention is of significant value in the field of medicine. By utilizing the combination of gel electrophoresis and MALDI MS malformed proteins can be very quickly found in the cells of certain organs or certain body fluids and the type of malformation can be very quickly established. These malformed proteins appear on the gel electrophoresis plate (after staining or using other methods of visualization) at places other than their usual ones so they can be very easily found, with computer programs already available. With the method presented here it is then possible to very quickly determine the type of protein malformation.

The invention is illustrated by the following Examples.

A solution of α-cyano-4-hydroxy-cinnamic acid in acetone was transferred to a clean metallic support by pipette and dispersed almost instantaneously because its surface tension is diminishingly low. One microliter of a virtually saturated solution was sufficient for about 4 square centimeters of surface, resulting in a solution film thickness of about 2.5 micrometers and a matrix layer thickness of about 300 to 600 nanometers after drying. This thickness has proved very favourable with respect to smoothness and electrical conductivity.

The solvent was evaporated in a clean current of air in less than 10 seconds, and the matrix layer obtained was thin, visually smooth, and lacquer-like. The matrix material α-cyano-4-hydroxy-cinnamic acid, which is highly soluble in acetone but barely soluble in pure water or in acidified methanol-water solution, has proved particularly advantageous for protein analyses. However, other matrix materials or solvents known to the expert can also be used with similar success.

The sample supports made in this way and having a thin matrix layer bind protein and other heavy molecules from solutions so firmly that they cannot be removed in subsequent washing processes with mildly acidified water or other washing liquids. The washing processes eliminate substances such as buffer salts, electrolytes, and other residues in the solution which interfere with the determination.

It is desirable to provide the preferably metallic sample supports with a non-electrically conductive lacquer border either before or after coating with the matrix layer. This border facilitates subsequent electrophoretic transfer of proteins because a short circuit with the metallic support at the border can be prevented.

The sample support with the smooth matrix layer can now be firmly pressed onto the moist gel plate or moist transfer membrane and kept there for a few minutes. This process on its own is sufficient to obtain scans. About 5 to 200 attomol of substance are transferred per separated protein, depending on the original concentration. About 50 attomol is adequate for a relatively good scan.

Adding a highly diluted solution of trifluoroacetic acid to the membranes increases yield slightly.

However, the most favourable method is for the proteins to be transported to the matrix layer by electrophoresis. By electrophoretic transport femtomol quantities can easily be transferred. Since overloading the matrix layer with proteins detracts from the ionization process, the loading of the matrix layer can be repeated a number of times without causing an excessive reduction of concentration in the original membrane. Various sample support plates with proteins from a single gel separation can be coated, either from different points on the gel plate or also from the same point because the quantity of protein is greater than required for the sample support plate.

By using the transfer membrane the proteins were cleaved ("digested") by enzymes in situ in a manner which is basically known. This process is called proteolysis. Subsequently the mixture of fragments was transferred to the matrix layer electrophoretically. Here too, about 50 to 100 attomol per fragment was sufficient, i.e. only 50 to 100 attomol of the original protein, to obtain scans of adequate quality which allow determination of the molecular weight of the fragments to better than one atomic unit of mass.

In particular several sample support plates can be loaded from a single gel separation on account of the high sensitivity of mass spectrometry. In doing so it is possible to load some sample supports with the uncut, original proteins and then other sample supports with enzymatically digested proteins. In this way both the molecular weights of the original proteins and the identity of the proteins can be determined by means of the enzyme fragments.

For scanning it is particularly advantageous to use a defocussed laser beam. From an application of 50 attomol of analysis substance it is possible to produce about 30 to 300 scans in consecutive laser bombardments, which are usually added together in order to enhance the signal-to-noise ratio. At a laser repetition frequency of 10 Hz the entire scan takes only three to thirty seconds per substance. At higher levels of concentration much shorter scanning times can be achieved.

The surface of the sample support was scanned with the mass spectrometer by moving the laser point (or by moving the sample support plate). The individual distributed proteins were then recognized by their scans. Where spots of protein overlap, mathematical methods of separation can be used to "deconvolute" the scans, as already developed for GC/MS techniques.

It is advisable to coat the matrix layer with reference substances of known molecular mass beforehand in order to obtain very accurate molecular determinations through this internal reference. With matrix layers coated in this way we have been able to achieve mass accuracies of about 20 ppm.

Very small quantities of one or more reference substances with known molecular weights can very easily be applied over large areas before the samples are applied. It is even possible to add the reference substances to the matrix solution.

The sample supports can be stored with matrix layers and reference substances for many weeks. There should be efficient exclusion of air because the highly adsorbent layers relatively quickly accumulate substances from the ambient air. It is also advisable to cool the supports in order to avoid recrystallisation of the microcrystalline layer recrystallizes in the course of time to form larger crystals.

While the invention has been shown and described with reference to the preferred embodiments thereof, it will be understood by those skilled in the art that various changes in form and detail may be made therein without departing from the spirit and scope of the invention as defined by the appended claims.

What is claimed is:

1. A method for the mass spectrometric analysis of an analyte substance in a sample which has been separated by gel electrophoresis on a gel electrophoresis plate, which method comprises:

coating a sample support plate with a smooth adsorptive layer of a solid matrix substance, the matrix substance being a material which can be coevaporated with the sample and which interacts with the sample in a gaseous phase so as to generate ions of the sample by ion-molecular reaction;

transferring the sample to the surface of the matrix layer of the sample support plate by direct contact with at least one of the electrophoresis plate and a moist transfer membrane, contact between the sample and matrix layer being such that substantially no dissolution of the matrix substance results therefrom; and ionizing the analyte substance by matrix-assisted laser desorption.

2. A method as claimed in claim 1, wherein the sample is transferred from the electrophoresis plate to the transfer membrane and is transferred from the transfer membrane to the sample support plate in a second step.

3. A method as claimed in claim 2, wherein the transfer membrane is a polyvinylidene difluoride membrane.

4. A method as claimed in claim 1, wherein the matrix layer of the sample support plate is made conductive by the incorporation therein of an electrically conductive substance.

5. A method as claimed in claim 1, wherein the sample is transferred to the sample support plate by electrophoresis.

6. A method as claimed in claim 1, wherein the gel electrophoresis is a two-dimensional electrophoresis.

7. A method as claimed in claim 1, wherein a diffusion adjuvant is employed to assist diffusion of the sample of analyte to the sample support.

8. A method as claimed in claim 7, wherein the diffusion adjuvant is dilute trifluoroacetic acid.

9. A method as claimed in claim 1, wherein the analyte substance is a protein.

10. A method as claimed in claim 9, wherein an amino acid chain of the protein is cleaved enzymatically prior to contact with the matrix layer.

11. A method as claimed in claim 10, wherein the enzymatic cleavage takes place in the gel electrophoresis plate, or in the transfer membrane.

12. A method as claimed in claim 10, wherein the enzymatic cleavage is carried out using trypsin.

13. A method as claimed in claim 1, wherein the transfer of the sample from the gel electrophoresis plate to a sample support plate is repeated a plurality of times, the said transfers being carried out to respective sample supports or to respective regions of the same sample support.

14. A method as claimed in claim 13, wherein after one or more sample transfers, a protein in a remaining sample is cleaved enzymatically and, subsequently, proteolytic fragments of the protein are transferred to the matrix.

15. A method as claimed in claim 1, wherein the matrix assisted laser desorption ionisation process is repeated at a plurality of points on the matrix surface.

* * * * *